(12) United States Patent
Ouchi

(10) Patent No.: US 6,193,737 B1
(45) Date of Patent: Feb. 27, 2001

(54) TREATING INSTRUMENT FOR OPERATIVE ENDOSCOPY

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/233,028

(22) Filed: Jan. 20, 1999

(30) Foreign Application Priority Data

Feb. 6, 1998 (JP) .................................................. 10-025373

(51) Int. Cl.[7] .................................................. A61B 17/32
(52) U.S. Cl. ............................................ 606/174; 606/145
(58) Field of Search .................................. 606/174, 172, 606/173, 175, 205, 206, 207–210, 170, 171, 145, 147, 148

(56) References Cited

U.S. PATENT DOCUMENTS

| 487,068 | * | 11/1892 | Drinkwater | 606/174 |
| 5,269,804 | * | 12/1993 | Bales et al. | 606/205 |
| 5,308,358 | * | 5/1994 | Bond et al. | 606/205 |
| 5,368,606 | * | 11/1994 | Marlow et al. | 606/170 |
| 5,921,984 | * | 7/1999 | Sutcu et al. | 606/46 |

FOREIGN PATENT DOCUMENTS

| 6114075 | 4/1994 | (JP) . |
| 6296619 | 10/1994 | (JP) . |
| 8140985 | 6/1996 | (JP) . |
| 8164141 | 6/1996 | (JP) . |

* cited by examiner

*Primary Examiner*—Michael Buiz
*Assistant Examiner*—Lien Ngo
(74) *Attorney, Agent, or Firm*—Greenblum & Bernstein P.L.C.

(57) ABSTRACT

A treating instrument for operative endoscopy has a pair of treating members provided at the distal end of a sheath. The pair of treating members are simultaneously opened or closed in a beaklike manner by remote control from the proximal end of the sheath. A driving device is provided at the distal end of the sheath for driving the pair of treating members to perform respective opening and closing actions through different rotation angles.

17 Claims, 6 Drawing Sheets

TREATING INSTRUMENT FOR OPERATIVE ENDOSCOPY

BACKGROUND OF THE INVENTION

The present disclosure relates to subject matter contained in Japanese Patent Application No. 10-25373 (filed on Feb. 6, 1998), which is expressly incorporated herein by reference in its entirety.

1. Field of the Invention

The present invention relates to a treating instrument for operative endoscopy that is inserted into a patient's body from a hole opened in the body surface and used under observation with an endoscope.

2. Description of the Prior Art

Many of treating instruments for operative endoscopy have a pair of treating members provided at the distal end of the insert part of an endoscope. The pair of treating members are opened or closed in a beaklike manner by remote control conducted at the proximal end of the insert part.

Such treating instruments for operative endoscopy include two different types: a bilaterally opening type in which both a pair of treating members are opened or closed in opposite directions through the same rotation angle; and a unilaterally opening type in which only one of a pair of treating members is rotatable to perform an opening and closing action, the other being fixed.

The unilaterally opening type is clumsy and likely to cause a misoperation because only one treating member is rotatable when the treating instrument is used to hold an affected part between the pair of treating members. For this reason, the bilaterally opening type is widely used.

When a treating instrument for operative endoscopy is inserted into a patient's body, if an affected part to be submitted to an operation lies on the front side of an organ, the above-described conventional bilaterally opening type of treating instrument can be effectively used. In such a case, the affected part can be readily held with the pair of treating members to perform the desired operation under endoscopic observation.

However, as shown in FIG. 6 by way of example, if an affected part 101 to be submitted to an operation lies behind an organ 100, it is difficult to hold the affected part 101 with a pair of treating members 51. Therefore, there are cases where the intended operation cannot smoothly be performed.

SUMMARY OF THE INVENTION

An object of the present invention is to provide a treating instrument for operative endoscopy designed so that even when an affected part to be treated is situated behind an organ, the affected part is readily held between a pair of treating members, thereby enabling an operation to be performed smoothly and safely under endoscopic observation.

Other objects and advantages of the present invention will become apparent from the following detailed description of illustrated embodiments of the invention.

According to the present invention, there is provided a treating instrument for operative endoscopy in which a pair of treating members are provided at the distal end of a sheath so that the pair of treating members are simultaneously opened or closed in a beaklike manner by remote control from the proximal end of the sheath. The treating instrument includes a driving device for driving the pair of treating members to perform respective opening and closing actions through different rotation angles. The driving device is provided at the distal end of the sheath.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENT

An embodiment of the present invention will be described below with reference to the accompanying drawings.

Figure 1:
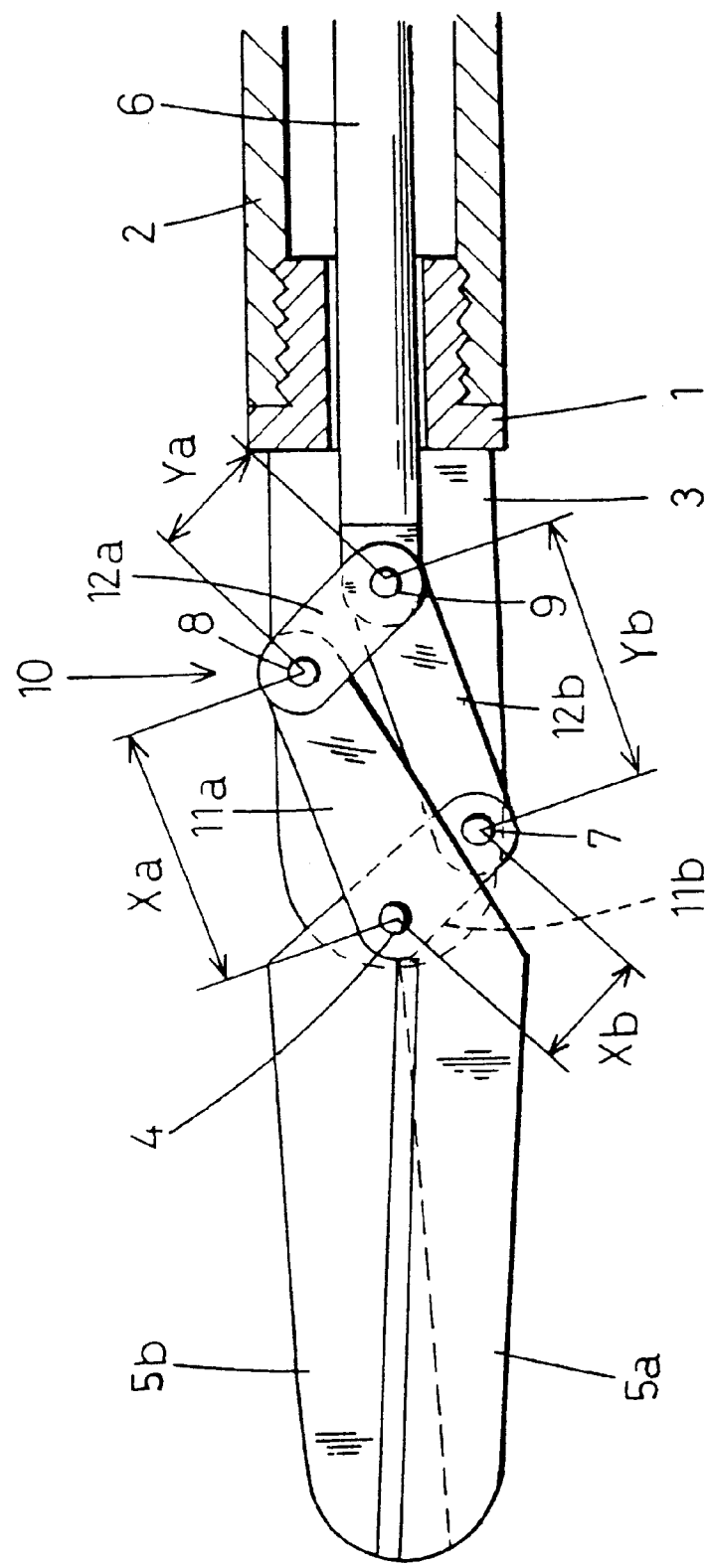
FIG. 1 is a sectional side view showing a distal end portion of a treating instrument for operative endoscopy according to a first embodiment of the present invention in a state where a pair of treating members are closed.

FIG. 1 shows a distal end portion of a pair of scissors for operative endoscopy to which the present invention is applied. A sheath (insert part) 2 is inserted into a patient's body from a hole opened in the body wall. The sheath 2 is formed from a rigid pipe. A distal end block 1 is connected to the distal end of the sheath 2 by thread engagement. The distal end block 1 has a large slit 3 cut from the forward end thereof.

A pivot shaft 4 is mounted on the distal end block 1 in such a way as to cross the distal end portion of the slit 3. A pair of treating members 5a and 5b are each rotatably supported by the pivot shaft 4. In this embodiment, the treating members 5a and 5b are two blades of a pair of scissors.

A link mechanism 10 for opening and closing the pair of treating members 5a and 5b is placed in the slit 3. The link mechanism 10 has four links 11a, 12a, 11b and 12b that are connected together so as to be rotatable relative to each other in the form of a pantograph.

Two forward links 11a and 11b in the link mechanism 10 are each integral and contiguous with the first treating member 5a or the second treating member 5b and rotatable about the pivot shaft 4.

Two intermediate links 12a and 12b are rotatably connected to the two links 11a and 11b through connecting shafts 7 and 8, respectively. The rear ends of the intermediate links 12a and 12b are rotatably connected to a control rod 6 by a connecting shaft 9.

The control rod 6 is axially movably inserted in the sheath 2. The control rod 6 is remote-controlled from the proximal end of the sheath 2 (the right-hand side as viewed in FIG. 1) to activate the link mechanism 10, thereby enabling the pair of treating members 5a and 5b to be opened or closed in a beaklike manner.

Of the four links 11a, 12a, 11b and 12b, which form the link mechanism 10, the link 11a connected to the first treating member 5a has a length Xa longer than the length Xb of the link 11b connected to the second treating member 5b. That is, Xa>Xb.

The length Ya of the intermediate link 12a connected to the first link 11a is shorter than the length Yb of the intermediate link 12b connected to the second link 11b. That is, Ya<Yb.

It should be noted that in this embodiment the lengths of the four links 11a, 12a, 11b and 12b are set to Xa=Yb and Xb=Ya. That is, the link mechanism 10 forms a parallelogram. However, the present invention is not necessarily limited thereto.

In the treating instrument for operative endoscopy according to this embodiment, which is arranged as stated above, when the link mechanism 10 is activated by moving the control rod 6 back and forth, the pair of treating members 5a and 5b are opened or closed simultaneously. At this time, the angle through which the second treating member 5b rotates is larger than the rotation angle of the first treating member 5a.

Figure 2:
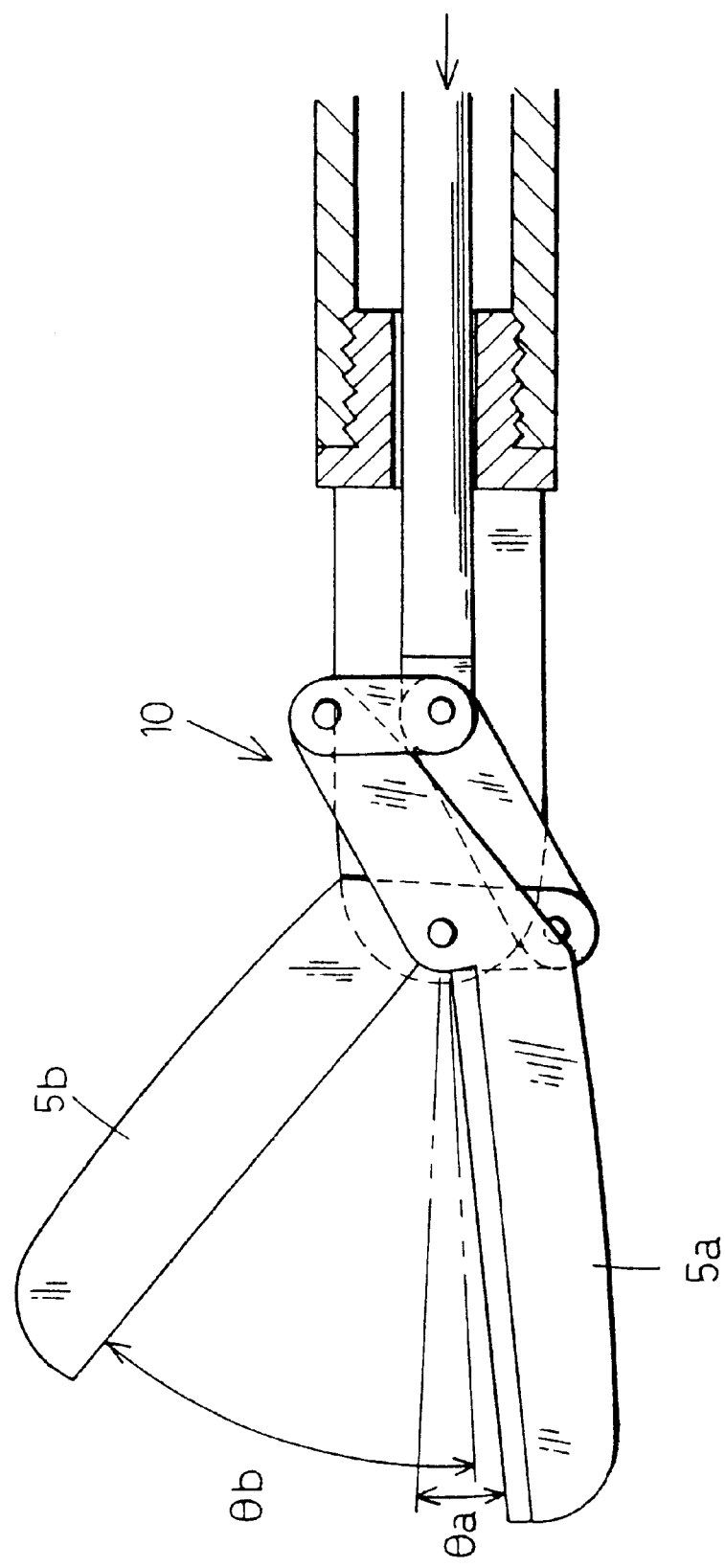
FIG. 2 is a sectional side view showing the distal end portion of the treating instrument for operative endoscopy according to the first embodiment of the present invention in a state where the pair of treating members are opened.

Accordingly, when the treating members 5a and 5b are closed as shown in FIG. 1, both the treating members 5a and 5b extend in the same direction as the axis of the sheath 2. When the treating members 5a and 5b are opened, as shown in FIG. 2, the opening angle θb of the second treating member 5b is larger than the opening angle θa of the first treating member 5a. That is, θa<θb.

It should be noted that θa≈7° and θb≈50°, and hence θb/θa≈7. The maximum opening angle $\theta_{max.}$ (θa+θb minus the overlapping angle of the two treating members 5a and 5b when closed) is $\theta_{max.}$≈55°.

However, the practical maximum opening angle $\theta_{max.}$ of the pair of treating members 5a and 5b is within the range of from 35° to 60°. θa and θb can be set in various combinations, including those shown below by way of example:

Example 1: θa≈11°, θb≈55°, θb/θa≈5, $\theta_{max.}$≈60°
Example 2: θa≈8°, θb≈32+, θb/θa≈4, $\theta_{max.}$≈35°
Example 3: θa≈6°, θb≈48°, θb/θa≈8, $\theta_{max.}$≈50°

Figure 3:
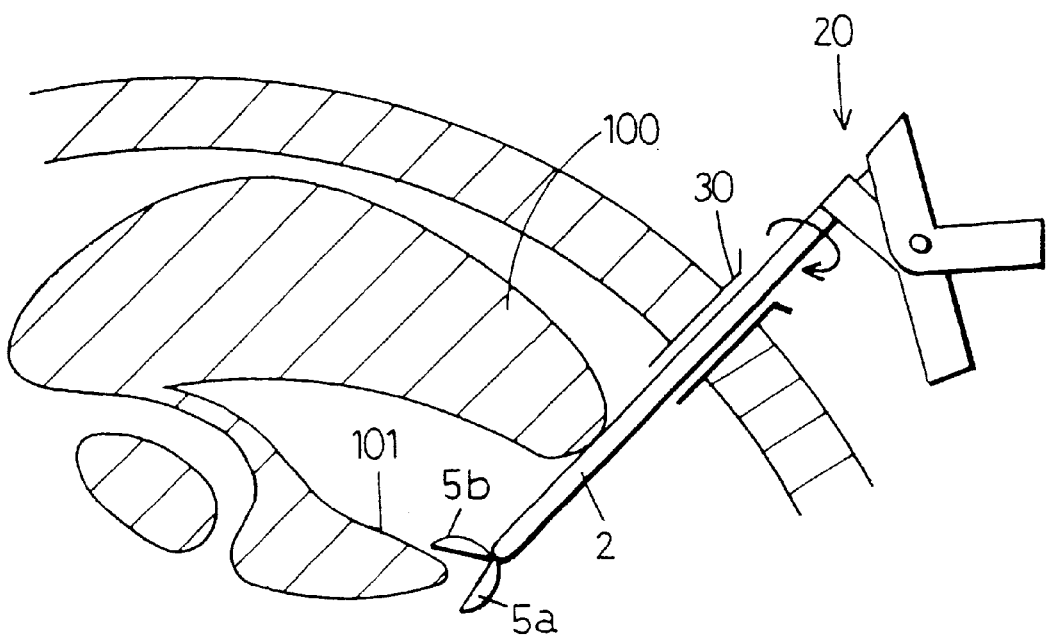
FIG. 3 is a schematic diagram showing the way in which the treating instrument for operative endoscopy according to the first embodiment of the present invention is actually used.

The treating instrument for operative endoscopy, which operates as described above, is easy to use because both the pair of treating members 5a and 5b are rotatable to perform an opening and closing action. That is, the treating instrument is of the bilaterally opening type. Moreover, even in a case where, as shown in FIG. 3, an affected part 101 to be submitted to an operation lies behind an organ 100, the treating members 5a and 5b can be opened in the direction of the affected part 101 to hold it therebetween. Thus, the affected part 101 can be readily submitted to an operation, e.g. cutting.

The opposing directions of the treating members 5a and 5b when opened can be changed by rotating the sheath 2 about its own axis at the proximal end thereof. Therefore, the treating instrument can be readily aimed at the affected part 101 simply by rotating the sheath 2 about the axis thereof. Reference numeral 20 in FIG. 3 denotes a control part connected to the proximal end of the sheath 2. Reference numeral 30 denotes a trocal for ensuring a hole opened in the body wall.

Figure 4:
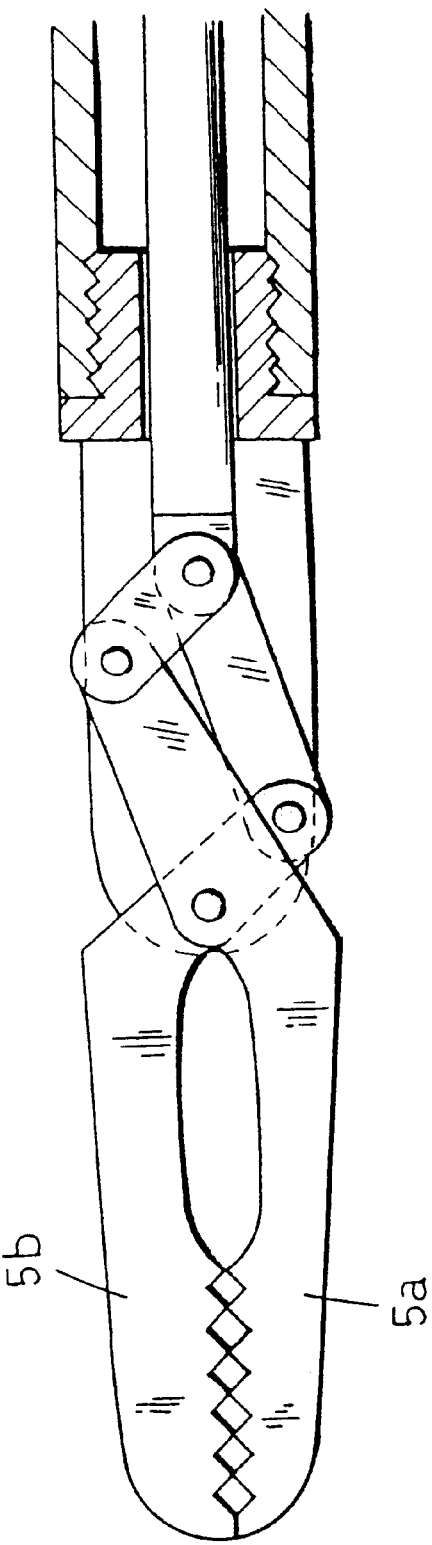
FIG. 4 is a sectional side view showing a distal end portion of a treating instrument for operative endoscopy according to a second embodiment of the present invention in a state where a pair of treating members are closed.
Figure 5:
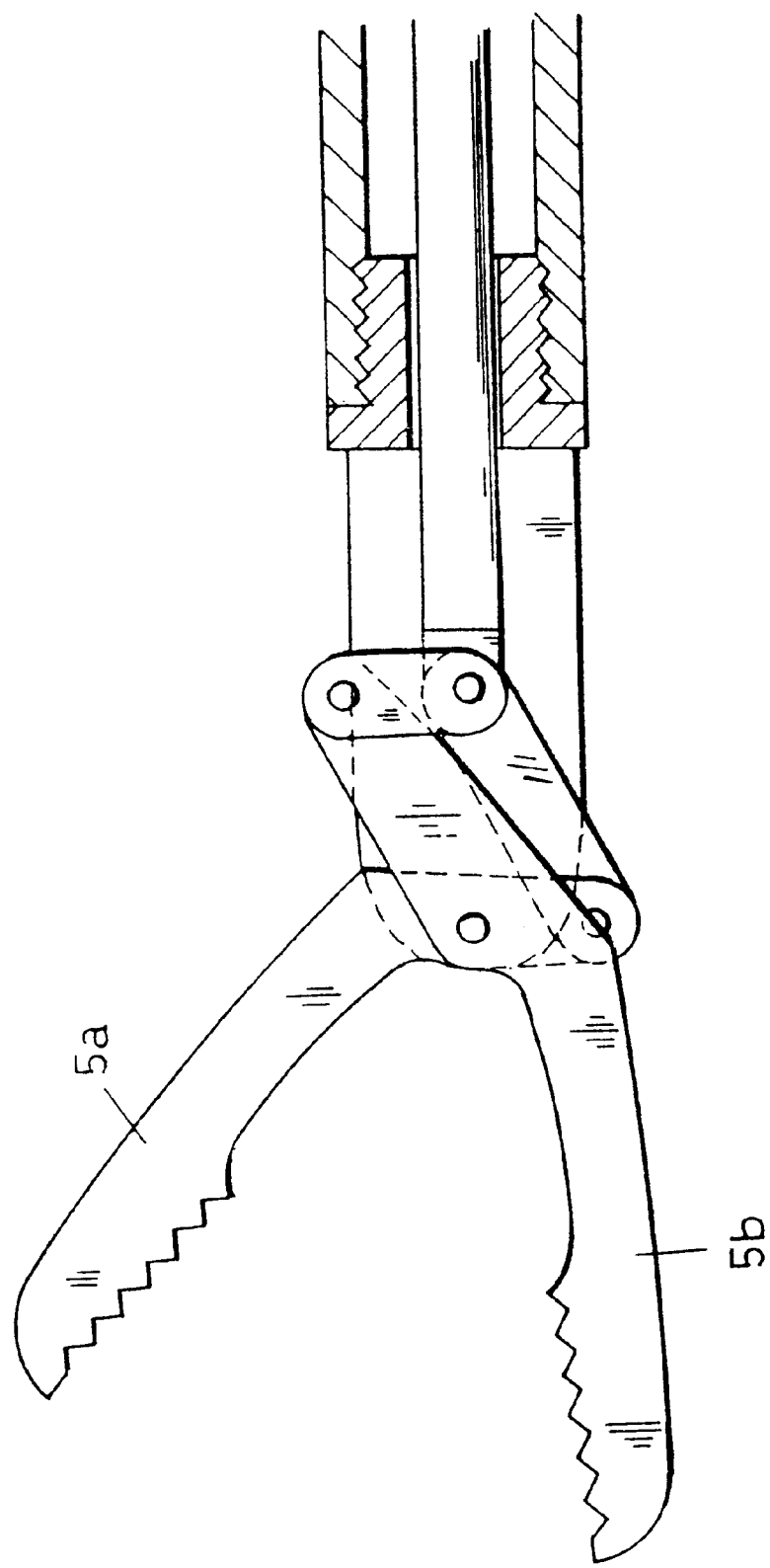
FIG. 5 is a sectional side view showing the distal end portion of the treating instrument for operative endoscopy according to the second embodiment of the present invention in a state where the pair of treating members are opened.
Figure 6:
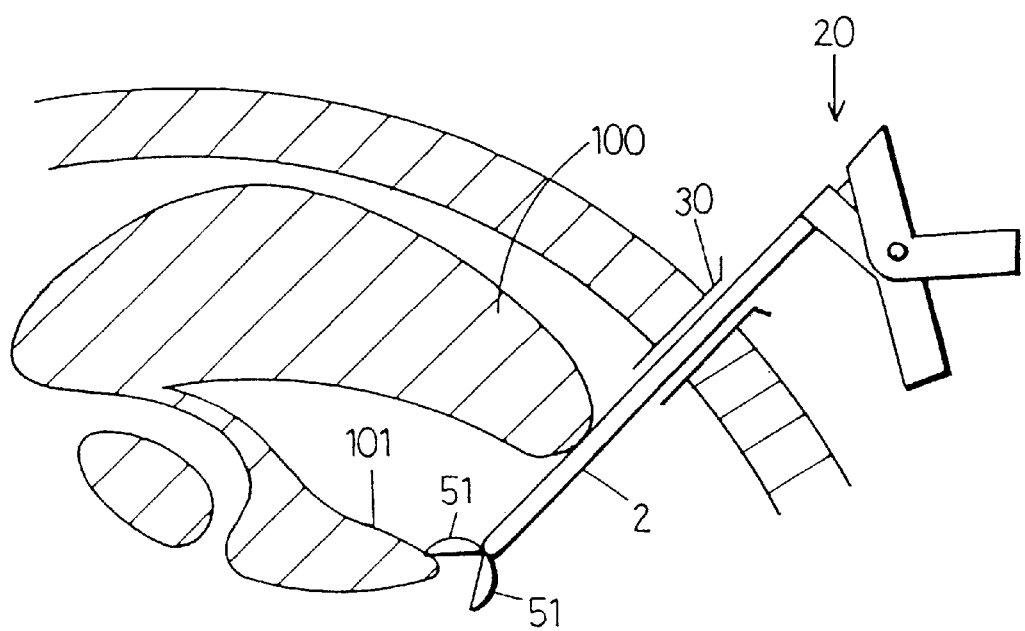
FIG. 6 is a schematic diagram showing the way in which a conventional treating instrument for operative endoscopy is actually used.

It should be noted that the present invention is not necessarily limited to the pair of scissors for operative endoscopy but can be applied to various other treating instruments for operative endoscopy. FIGS. 4 and 5 show a second embodiment in which the present invention is applied to a holding forceps for operative endoscopy. In FIG. 4, a pair of grasping members provided as treating members 5a and 5b are closed. In FIG. 5, the pair of grasping members are open.

According to the present invention, a pair of treating members provided at the distal end of a sheath are opened or closed through different rotation angles. Therefore, even when an affected part to be submitted to an operation lies behind an organ, the pair of treating members can be readily opened in the direction of the affected part to hold it therebetween. Therefore, the desired operation can be performed smoothly and safely under endoscopic observation. Moreover, the treating instrument is easy to use because it is of the bilaterally opening type.

While the invention has been described by reference to specific embodiments chosen for purposes of illustration, it should be apparent that numerous modifications could be made thereto by those skilled in the art without departing from the basic concept and scope of the invention.

What is claimed is:

1. A treating instrument for operative endoscopy comprising:
a pair of treating members, said pair of treating members being positioned at a distal end of a sheath said pair of treating members being simultaneously openable and closable in a beaklike manner by remote control from a proximal end of said sheath;
a driving mechanism that drives said pair of treating members to insure performance of respective opening and closing operations through different rotation angles, said driving mechanism being provided at the distal end of said sheath.

2. A treating instrument for operative endoscopy according to claim 1, wherein said driving mechanism is a pantograph-shaped link mechanism connected to said pair of treating members, said link mechanism having a link connected to one of said pair of treating members and another link connected to the other of said pair of treating members, said links having different lengths, so that said pair of treating members are driven to perform respective opening and closing actions through different rotation angles.

3. A treating instrument for operative endoscopy according to claim 2, wherein said link mechanism has approximately a parallelogram shape.

4. A treating instrument for operative endoscopy according to claim 1, wherein a ratio of the rotation angle of one of said pair of treating members to the rotation angle of the other is in a range of from 4 to 8.

5. A treating instrument for operative endoscopy according to claim 4, wherein a ratio of the rotation angle of one of said pair of treating members to the rotation angle of the other is in a range of from 5 to 7.

6. A treating instrument for operative endoscopy according to claim 1, wherein a maximum opening angle of said pair of treating members is in a range of from 35 degrees to 60 degrees.

7. A treating instrument for operative endoscopy according to claim 1, wherein when closed, said pair of treating members extend in a same direction as an axis of said sheath.

8. A treating instrument for operative endoscopy according to claim 1, wherein said pair of treating members turn as said sheath is rotated about its axis at the proximal end thereof.

9. A treating instrument for operative endoscopy according to claim 1, wherein said sheath is a rigid pipe.

10. A treating instrument for operative endoscopy according to claim 1, wherein said treating members are two blades of a pair of scissors.

11. A treating instrument for operative endoscopy according to claim 1, wherein said treating members are grasping members.

12. The treating instrument according to claim 1, said pair of treating members having a common pivot, a distance between said common pivot and a connection to said driving mechanism being different for each of said pair of treating members.

13. The treating instrument according to claim 1, said driving mechanism including a common pivot adjacent to said sheath, links of different length being connected to said common pivot and to each of said pair of treating members.

14. The treating instrument according to claim 12, said treating members comprising blades of a pair of scissors.

15. The treating instrument according to claim 12, said treating members comprising a pair of grasping members.

16. The treating instrument according to claim 13, said treating members comprising blades of a pair of scissors.

17. The treating instrument according to claim 13, said treating members comprising a pair of grasping members.

* * * * *